(12) United States Patent
Wong et al.

(10) Patent No.: US 10,028,965 B2
(45) Date of Patent: Jul. 24, 2018

(54) USE OF SUSTAINED RELEASE DEXAMETHASONE IN POST-CATARACT SURGERY INFLAMMATION

(71) Applicant: Icon Bioscience, Inc., Sunnyvale, CA (US)

(72) Inventors: Vernon G. Wong, Menlo Park, CA (US); William S. White, Birmingham, AL (US); Mae W. Hu, Los Altos Hills, CA (US); Glenn T. Huang, Fremont, CA (US); Faina Karasina, Mountain View, CA (US)

(73) Assignee: ICON BIOSCIENCE, INC., Newark, CA (US)

( * ) Notice: Subject to any disclaimer, the term of this patent is extended or adjusted under 35 U.S.C. 154(b) by 0 days.

(21) Appl. No.: 14/893,381

(22) PCT Filed: May 23, 2014

(86) PCT No.: PCT/US2014/039319
§ 371 (c)(1),
(2) Date: Nov. 23, 2015

(87) PCT Pub. No.: WO2014/190248
PCT Pub. Date: Nov. 27, 2014

(65) Prior Publication Data
US 2016/0120879 A1    May 5, 2016

Related U.S. Application Data

(60) Provisional application No. 61/827,091, filed on May 24, 2013.

(51) Int. Cl.
| *A61K 31/573* | (2006.01) |
| *A61K 9/00* | (2006.01) |
| *A61K 47/14* | (2017.01) |

(52) U.S. Cl.
CPC .......... *A61K 31/573* (2013.01); *A61K 9/0048* (2013.01); *A61K 47/14* (2013.01)

(58) Field of Classification Search
CPC ..... A61K 31/573; A61K 9/0048; A61K 47/14
See application file for complete search history.

(56) References Cited

U.S. PATENT DOCUMENTS

| 4,211,793 A | 7/1980 | Lodhi et al. |
| 4,727,109 A | 2/1988 | Schmidt et al. |
| 4,889,845 A | 12/1989 | Ritter et al. |
| 5,635,190 A | 6/1997 | Cheetham et al. |
| 5,747,058 A | 5/1998 | Tipton et al. |
| 6,468,559 B1 | 10/2002 | Chen et al. |
| 6,960,346 B2 | 11/2005 | Shukla et al. |
| 7,560,120 B2 | 7/2009 | Shukla et al. |
| 7,906,136 B2 | 3/2011 | Wong et al. |
| 8,242,099 B2 | 8/2012 | Wong et al. |
| 8,313,763 B2 | 11/2012 | Margaron et al. |
| 8,541,413 B2 | 9/2013 | Wong et al. |
| 9,011,915 B2 | 4/2015 | Wong et al. |
| 9,016,221 B2 | 4/2015 | Brennan et al. |
| 9,149,439 B2 | 10/2015 | Patel et al. |
| 9,289,428 B2 | 3/2016 | Wong et al. |
| 2003/0216303 A1 | 11/2003 | Ambuhl et al. |
| 2004/0024006 A1 | 2/2004 | Simon |
| 2004/0253293 A1 | 12/2004 | Shafiee et al. |
| 2006/0073182 A1 | 4/2006 | Wong et al. |
| 2008/0038316 A1 | 2/2008 | Wong et al. |
| 2009/0017085 A1 | 1/2009 | Cilurzo et al. |
| 2009/0136445 A1 | 5/2009 | Wong et al. |
| 2010/0331966 A1 | 12/2010 | Borck |
| 2011/0111006 A1 | 5/2011 | Wong et al. |
| 2011/0160645 A1 | 6/2011 | Sutermeister et al. |
| 2014/0180245 A1 | 6/2014 | Wong et al. |
| 2015/0273066 A1 | 10/2015 | Wong et al. |
| 2016/0095818 A1 | 4/2016 | Hugerth et al. |

FOREIGN PATENT DOCUMENTS

| WO | 2002/00137 A1 | 1/2002 |
| WO | 2012/149040 A2 | 11/2012 |
| WO | 2013/036309 A2 | 3/2013 |

OTHER PUBLICATIONS

International Search Report and Written Opinion dated, Sep. 11, 2014, cited in related International Application No. PCT/US2014/039319.
International Preliminary Report on Patentability, dated Dec. 3, 2015, issued in related International Patent Application No. PCT/US2014/039319, filed May 23, 2014.
Chang, et al., Intracameral dexamethasone reduces inflammation on the first postoperative day after cataract surgery in eyes with and without glaucoma, Clinical Ophthalmology (2009) 3(1):345-355.
Extended European Search Report dated, Dec. 2, 2016, in related EP Application No. 14800446.8, filed May 23, 2014.
An, J.A. et al., "Evaluation of eyedrop administration by inexperienced patients after cataract surgery," J. Cataract Refract. Surg. 2014; 40:1857-1861.

(Continued)

*Primary Examiner* — Sudhakar Katakam
(74) *Attorney, Agent, or Firm* — Medler Ferro Woodhouse & Mills PLLC

(57) ABSTRACT

The present embodiments provide for a treatment regimen and use of a short-term sustained release liquid formulation of dexamethasone in citrate, wherein a single administration of a minute dosage form into the anterior chamber of the eye provides for anti-inflammatory therapy following cataract surgery.

11 Claims, 5 Drawing Sheets

(56) References Cited

OTHER PUBLICATIONS

Kwak. H.W. et al., "Evaluation of the retinal toxicity and pharmacokinetics of dexamethasone after intravitreal injection," Arch. Ophthalmol. 1992; 110(2):259-266.
McGhee, C.N., "Pharmacokinetics of ophthalmic corticosteroids," Br. J. Ophthalmol. 1992; 76:681-684.

USE OF SUSTAINED RELEASE DEXAMETHASONE IN POST-CATARACT SURGERY INFLAMMATION

RELATED APPLICATION

This application is related to and claims priority benefit of U.S. Application No. 61/927,091, filed May 24, 2013, incorporated fully herein by reference.

BACKGROUND

A cataract is clouding of the lens of the eye, which impedes the passage of light. Most cataracts are related to ageing, but occasionally children are born with the condition; or the cataract may develop after an injury, inflammation, or disease. Risk factors for age-related cataracts include diabetes, prolonged exposure to sunlight, tobacco use, and excessive alcohol consumption.

Vision can be restored by surgically removing the affected lens, and in most cases replacing it by an artificial one. Indeed, in Western countries the rate of cataract surgery has increased significantly during the past two decades. In many countries, cataract surgery now accounts for over half of all ophthalmic surgery and has become the most common elective surgical procedure. Although today the removal of the opaque lens and its replacement with an artificial one represents a routine operation that involves only minor risks, it consumes a considerable share of the resources for ophthalmic care. Minimizing the side effects of cataracts procedures and impact of the health care system remains an important goal.

In addition to antibiotic eye drops to prevent infection, anti-inflammatory eye drops are also prescribed to help reduce any internal inflammation. These eye drops are in some cases started before surgery, and in some cases must be continued for 2 or 3 months. Compliance with dosing and application regimens in order to minimize the side effects of inflammation can be challenging for many patients. The quicker any inflammation is resolved the quicker the patient realizes the full desired therapeutic outcome of the surgery and can resume normal daily activities. Additionally, the use of eye drops to delivery medication into the eye is at best marginally effective. In most cases only a small percentage of the dose actually enters the eye. This factor along with compliance issues limit the effective drug levels that can be achieved using eye drop technology. Therefore, there is a need for sustained release anti-inflammation therapy that can benefit the cataract patient by replacing the need for anti-inflammatory eye drops. In particular, there is a need for a formulation and method that delivers highly effective drug levels without the issues associated with eye drops, which formulation results in superior clinical results.

SUMMARY

The present embodiments provide for the post-cataract surgery use of an easily injectable, short-term sustained release formulation for sustained release of the anti-inflammatory drug dexamethasone for about one to three weeks. In one embodiment, the formulation consists essentially of dexamethasone in a citrate vehicle, in which one dose volume ranging from about 1 µL to about 12 µL of a formulation consisting essentially of dexamethasone at a concentration ranging from about 1% to about 20% (w/w) in about 80% to about 99% citric acid ester or a citric acid ether, is injected into the anterior chamber of the eye for treating inflammation after cataract surgery. In particular example embodiments, a patient having undergone cataract surgery is administered about 5 µL of a formulation consisting of about 6%, about 9% or about 12% (w/w) dexamethasone in triethyl acetyl citrate, which is injected into the anterior chamber of the eye. In use, inflammation is controlled post-cataract surgery by this single, minute volume injection. The present medication regimen replaces steroidal eye drops and provides improved benefit in ease of treatment, patient compliance, and clinical outcome for cataract surgery patients.

An aspect of the present embodiments provides for use of a formulation consisting of about 1 µL to about 12 µL of a composition consisting essentially of about 1% to about 20% (w/w) dexamethasone and about 80% to about 99% (w/w) triethyl acetyl citrate, that is administered as a single dose by injection into the anterior chamber of eye for the treatment of inflammation following cataract surgery, wherein said dosage form releases dexamethasone for at least 3 days as measured in saline solution under infinite sink conditions. In particular embodiments, the formulation of said use includes about 6% (w/w) dexamethasone; about about 9% (w/w) dexamethasone; or about 12% (w/w) dexamethasone. In another embodiment, the use of the formulation results in an anterior chamber cell count below 2 within 30 days of administration when assessed by slit lamp microscopy. In yet another embodiment, the use of the formulation comprises an injection delivered using a needle; or an injection delivered using a cannula.

Another aspect of the embodiments provides for a unit dosage consisting essentially of about 1% to about 20% (w/w) dexamethasone and about 80% to 99% triethyl acetyl citrate, wherein said dosage form releases dexamethasone for at least 3 days, as measured in saline solution under infinite sink conditions. In some embodiments, the unit dosage form comprises about 200 µg to about 800 µg of dexamethasone; about 342 µg of dexamethasone; about 517 µg of dexamethasone; or about 697 µg of dexamethasone. In other embodiments, the total volume of said unit dosage form is about 1 µL to about 12 µL; about 4 µL to about 6 µL; or about 5 µL. In other embodiments, the unit dosage form releases dexamethasone for at least 7 days, as measured in saline solution under infinite sink conditions. In particular embodiments, the unit dosage form releases said dexamethasone for at least 7 days, but no more than 35 days, as measured in saline solution under infinite sink conditions. In other embodiments, the unit dosage form retains at least 30% of its dexamethasone after 3 days, as measured in saline solution under infinite sink conditions.

Another embodiment provides for a unit dosage for the treatment of inflammation following cataract surgery consisting of a unit dose of about 5 µL of a formulation consisting essentially of either 342 µg, 517 µg or 697 µg dexamethasone in triethyl acetyl citrate, wherein the unit dose is injected into the anterior chamber of the eye following cataract surgery, and wherein administration results in an anterior chamber cell count below 2 within 30 days of administration when assessed by slit lamp microscopy.

Another aspect of the present embodiments provides for a kit comprising a pre-filled syringe or pre-filled vial containing a formulation consisting essentially of dexamethasone and triethyl acetyl citrate in a w/w dexamethasone: triethyl acetyl citrate ratio of about 6:94, about 9:91, or about 12:88; and injection syringe, a 25 gauge cannula or 28 gauge needle or 30 gauge needle that is, optionally, connected to the syringe; a dose loading guide; optionally, a dose delivery guide; and instructions for administration; wherein a single unit dose of about 5 μL of the formulation of the kit is injected into the anterior chamber of the eye for treating inflammation following cataract surgery.

Still another aspect of the embodiments provides for a method of treating inflammation following cataract surgery in a patient in need thereof, comprising injecting into the anterior chamber of the eye of the patient about 1 μL to about 12 μL of a composition consisting essentially of about 1% to about 20% (w/w) dexamethasone and about 80% to about 99% (w/w) triethyl acetyl citrate. In some embodiments of this aspect, the administration results in an anterior chamber cell count below 2 within 30 days of administration, when assessed by slit lamp microscopy; or the administration results in an anterior chamber cell count below 3 within 8 days of administration, when assessed by slit lamp microscopy. In other embodiments, the composition releases dexamethasone for at least 3 days, as measured in saline solution under infinite sink conditions. In other embodiments, the composition of the method includes about 200 μg to about 1100 μg of dexamethasone; about 342 μg of dexamethasone; about 517 μg dexamethasone; or about 697 μg dexamethasone. In still other embodiments of the method, the total dose volume of the composition is about 4 μL to about 7.5 μL.

Another aspect of the present embodiments provides for a unit dosage form comprising a prefilled syringe comprising about 1 μL to about 12 μL of a composition consisting of 1% to 20% (w/w) dexamethasone and 80% to 99% (w/w) triethyl acetyl citrate, wherein said dosage form releases said dexamethasone for at least 3 days but no more than 35 days as measured in saline solution under infinite sink conditions.

DETAILED DESCRIPTION

Figure 1:
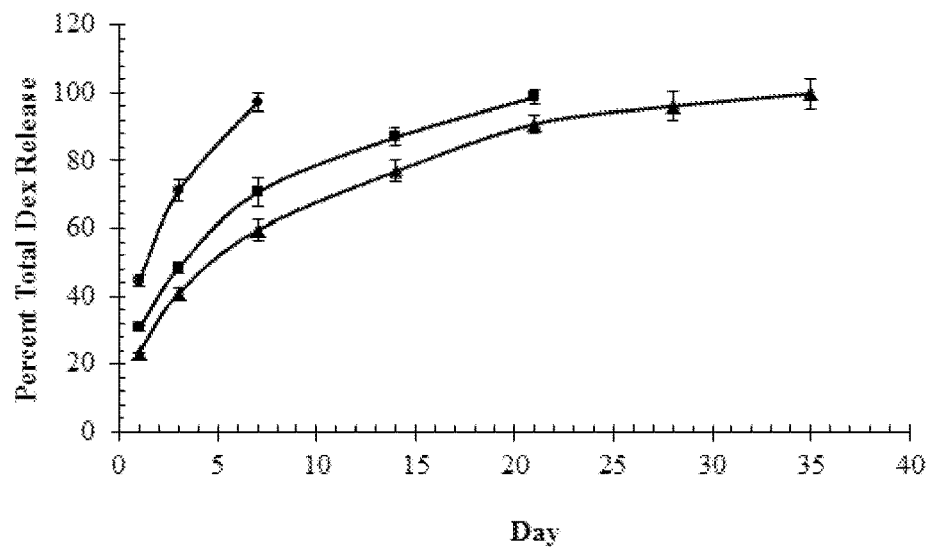
FIG. 1 shows the average in vitro dexamethasone (Dex) release from 5 μL aliquots of three formulations of Dex in triethyl acetyl citrate (ATEC), as a percent of Dex release per day in a 10 mL saline infinite sink, n=6: ●342 μg/5 μL; ■517 μg/5 μL; ▲697 μg/5 μL.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims. Unless defined otherwise, all technical and scientific terms used herein have the same meaning as those commonly understood to one of ordinary skill in the art to which this invention pertains.

As used herein and in the claims, the singular forms "a," "an," and "the" include the plural reference unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" in relation to percentages, generally means ±1%. "Consisting essentially of" means that the formulations described herein can contain additional ingredients that do not interfere with effectiveness of the drug product or drug release; or, in general, the formulations may contain additional ingredients that total less than 1%, 0.5% or 0.1% of the formulation, or are present in trace amounts.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Currently cataract surgery is accompanied by a lengthy and messy regimen of eye drops that are required to reduce inflammation in the eye. For example, following cataract surgery, prednisolone eye drops are typically applied four times daily for the first week, three times daily for the second week, two time daily for the third week, and once daily for the fourth week and beyond until the bottle runs dry. Additionally and concurrently, ketorolac eye drops are applied four times daily for the first through the fourth weeks following cataract surgery. These anti-inflammatory eye drops are used along with other eye drops such as antibiotic eye drops. The anti-inflammatory eye drops are sometimes opaque and render vision blurry. They are also messy, as the eye floods with drops and insoluble components collect in the corner of the eyes or on the eye lids. Moreover, many individuals have trouble applying these drops formulations correctly, with the right amount of dosing at the right time, for the correct length of weeks. In other words, beyond the inconvenience of such eye drops, compliance in the eye drops dosing regimen can be an issue.

The present embodiments provide for the use of an anti-inflammatory formulation in treating an acute inflammatory response to a surgical event. In particular, the present embodiments relate to the treatment of inflammation following cataract surgery comprising, in a particular embodiment, injecting into the anterior chamber of the eye a small volume, for example a dose form having a volume of about 4 µL, to about 12 µL, of a liquid formulation consisting essentially of dexamethasone in citrate, for example triethyl acetyl citrate. Although the release is sustained release, the dosage form herein provides for relatively short-term sustained release of the active drug, lasting from about one to three weeks. By design, the formulation delivers a relatively high dose of dexamethasone very quickly to give a quick response; it then tapers off quickly to minimize the potential of any adverse events associated with the use of steroids. This liquid formulation maintains a single, generally spherical bolus shape (a monolithic shape or cohesive structure), at the site of placement; is biocompatible, biodegradable; provides for the sustained release of dexamethasone; then disappears entirely after delivering dexamethasone to the desired site. The formulations provide for novel post-cataract surgery therapy that is manipulated easily and injected by qualified medical practitioners, and can be used instead of the current anti-inflammatory eye drops regimen or solid implants. This use avoids the inconvenience and compliance issues associated with the current anti-inflammatory eye drops regimen, by replacing it with a physician-administered, one-time application that assures correct dosing, compliance, and provides beneficial anti-inflammatory therapy following cataract surgery.

Dexamethasone is an anti-inflammatory glucocorticoid. Its chemical names include (11β,16α)-9-Fluoro-11,17,21-trihydroxy-16-methylpregna-1,4-diene-3,20-dione; 9α-Fluoro-16α-methylprednisolone; and 16α-mehtyl-9α-fluoro-1,4-pregnadiene-11β,17α,21-triol-3,20-dione. Pharmaceutical formulations of dexamethasone include dexamethasone, dexamethasone acetate and dexamethasone sodium phosphate. Thus, the term dexamethasone refers to dexamethasone salts, acids, variants, polymorphs, derivatives, prodrugs and metabolites, etc., that have (or will have) regulatory approval for use as anti-inflammatories for use in the eye.

Citrates, as used herein, include citric acid esters or citric acid ethers such as triethyl citrate (TEC), acetyl triethyl citrate (ATEC) and tributyl citrates such as acetyl tributyl citrate (ATBC) and tributyl citrate (TBC). Citrates vary in hydrophilicity or hydrophobicity, and citrates may be used in combination. Active agents can be dissolved, dispersed, emulsified or suspended in citrates and form liquids, gels or solids depending on the citrate(s) and active agents used in a particular formulation. In vitro and animal in vivo studies have reported the use of various citrates as sustained release vehicles. See U.S. Pat. No. 7,906,136, No. 7,560,120, No. 6,960,346; U.S. Patent Appl. Pub. No. 2011/0111006. A particularly useful citrate for the short-term sustained release of dexamethasone in the anterior chamber of the eye is acetyl triethyl citrate (also called ATEC, triethyl acetyl citrate, TEAC, triethyl O-acetyl citrate, or 1,2,3-Propanetricarboxylic acid,2-(acetyloxy)-triethyl ester).

Embodiments of the present invention use a citrate vehicle, in particular ATEC, as the delivery vehicle for dexamethasone in the treatment of inflammation following surgery for cataract(s). The dose volume of the formulation administered into the eye is relatively minute, in a range of from about 1 µL to about 12 µL, inclusive, for example, about 3 µL to about 10 µL, about 2.5 µL to about 7.5 µL, or about 4 µL to about 6 µL, inclusive, such as about 5 µL, about 7.5 µL or about 10 µL as a single dose delivered into the eye by injection.

The amount of dexamethasone in the formulation can be expressed in strength, such as from about 100 micrograms (µg) to about 1100 µg per dose, inclusive, for example about 200 µg to about 800 µg, about 300 µg to about 750 µg, about 300 µg to about 400 µg, about 500 µg to about 600 µg, and about 650 µg to about 750 µg, inclusive, such as about 114 µg, about 342 µg, about 513 µg, about 517 µg, about 684 µg, about 697 µg about 776 µg, or about 1046 µg. The amount of dexamethasone in the formulation can also be expressed as a range in concentration of from about 1% to about 45% dexamethasone (w/w), inclusive, for example, about 2% to about 35%, about 3% to about 25%, about 3% to about 20% about 5% to about 15%, about 4% to about 14% (w/w) dexamethasone, inclusive, such as about 1%, 4.5%, 6%, 9% or 12% (w/w) dexamethasone. The amount of in a citrate vehicle, such as ATEC, in the formulation can range from about 55% to about 99% (w/w) citrate, inclusive, for example, about 65% to about 85%, about 75% to about 97%, about 80% to about 97%, about 85% to about 95%, about 86% to about 96%, inclusive, such as about 91%, about 94%, or about 88%.

In other words, it is possible to design a dosage form in which a volume of about 4 µL to about 12 µL consists essentially of from 1% to 45% dexamethasone in corresponding 55% to 99% citrate. Thus, in a formulation consisting essentially of dexamethasone and ATEC, the weight ratio of dexamethasone:ATEC can be about 1:99, about 3:97, about 4:96, about 4.5:95.5, about 6:94, about 9:91, about 12:88, or about 20:80, inclusive. More specifically, for a low dose formulation consisting of 6% dexamethasone, a 5 µL dose weighs 5.7 mg, and contains 0.342 mg dexamethasone and 5.358 mg ATEC; for a medium dose of 9% dexamethasone, a 5 µL dose weighs 5.75 mg, and contains 0.5175 mg dexamethasone and 5.2325 mg ATEC. Alternative dosage forms include, for example, the following amounts of dexamethasone in the given dose volume: about 342 µg/about 5 µL, about 517 µg/about 5 µL, about 697 µg/about 5 µL, about 1046 µg/about 7.5 µL, about 776 µg/about 7.5 µL, about 513 µg/about 7.5 µL, about 513 µg/about 10 µL, about 684 µg/about 10 µL, or about 114 µg/about 10 µL.

A single administration of the dosage form, for example about 5 µL, about 7.5 µL or about 10 µL, into the anterior chamber of the eye can alleviate inflammation and replace the current eye drops regimen or the need for solid implants in patients in need thereof, i.e., following cataract surgery.

After the cataract surgery—any type of cataract surgery, such as phacoemulsification or extracapsular cataract surgery—is completed, the formulation is administered into the anterior segment through a small gauge cannula or needle. The dosage form can be placed in the anterior segment of the eye, either in front of or behind the iris, and the dosage form does not interfere with the patient's vision. The formulation can be administered using a cannula and vial, a prefilled vial, or prefilled syringe. A small gauge cannula and syringe can be used for administration behind the iris, but a small gauge needle can also be used, especially for injection in front of the iris. For example, at 25 gauge cannula (e.g., single use, anterior chamber cannula, 25 gauge, 8 mm, bend to tip from MST Precision Specialty Instruments, Phoenixville, Pa.) or 28 or 30 gauge needle are suitable to administer the dosage form, for example from about 4 µL to about 12 µL, inclusive, such as about 5 µL about 7.5 µL, or about 10 µL into the anterior chamber. Because the formulation retains its monolithic shape after injection, the physician can view proper placement of the formulation dosage form. After administration, as the dexamethasone is delivered by sustained release from the dosage form, the formulation disappears leaving behind nothing. The use of one administration of about 4 µL to about 12 µL of this dexamethasone formulation is sufficient to provide relief from inflammation following cataract surgery, and is may be used without the use of additional anti-inflammatory therapy such as steroidal or non-steroidal anti-inflammatory eye drops or solid implants.

A dosing guide for a syringe can be used to accurately load and deliver the minute volume of the present regimen. See WO 2012/149040. Briefly, an injection syringe is filled in excess of the volume required for the correct dose, and a spacer that is configured to regulate the dose loaded into the syringe is inserted abutting the plunger rod of the syringe at the top of the barrel of the syringe (the proximal end of the syringe) in between the grip-end of the plunger, and the excess formulation expelled until the spacer impedes further axial distal motion of the plunger. This physical mechanism relieves the user from having to visually determine or "eye-ball" the correct dose volume loaded in the syringe. The dose loading spacer guide can then be removed from the syringe device. Because many syringes comprise elastomeric gaskets as seals at the proximal end of the syringe barrel such that individual user strength in depressing the plunger can lead to variation in the a dose delivered, a dose dispensing guide can be placed on the plunger (or has already been placed on the syringe plunger "as sold"), which guide is configured generally as a "ring" that physically impedes further depression of the plunger after the correct dose volume has been delivered into the eye. Syringe loading and dosing guides have been made commercially (Berlin Food & Lab Equip., South San Francisco, Calif.; Encore Machining, San Jose, Calif.), and specifications are designed for the particular syringe and dose volume. For example, using such dosing and delivery guides, minute amounts of medicament, such as about 5.0 µL or about 7.5 µL, can be placed into the eye, depending on the size guide(s) used. Syringes suitable for use in delivering the formulations include disposable insulin syringes with permanently attached needles, particularly a 0.3 mL sterile insulin syringe (Becton Dickenson), or a sterile single-use glass syringe without attached needle, such as a 0.5 ml glass syringe (Hypak by Becton Dickenson). In one embodiment, the formulation, syringe, cannula or needle, dose loading guide and, optionally, dose delivery guide are included in a kit for accurate administration of the formulation dose unit.

The administration of a single dose of the formulation consisting essentially of dexamethasone in citrate has been observed to adequately control (prevent or ameliorate) inflammation following cataract surgery in humans. Thus, a particular embodiment of the present invention provides for the use of a dosage form of about 5 µL of a formulation consisting essentially of dexamethasone and ATEC in a single administration into the anterior chamber for the treatment of inflammation in the human eye following cataract surgery. The dexamethasone can be present in the particular embodiment is in the concentration of example, about 6%, about 9% or about 12% (w/w). As examples, the dexamethasone can be in an amount of about 342 µg, about 517 µg, or about 697 µg in the dosage form volume of about 5 µL delivered into the anterior chamber of the eye. More specifically, for a low dose formulation consisting of 6% dexamethasone, a 5 µL dose weighs 5.7 mg, and contains 0.342 mg dexamethasone and 5.358 mg ATEC; for a medium dose of 9% dexamethasone, a 5 µL dose weighs 5.75 mg, and contains 0.5175 mg dexamethasone and 5.2325 mg ATEC. These dosage forms are injected only once: at the time of cataract surgery, after the surgery is complete and while the patient is still under anesthesia (local or systemic anesthesia). The administration is done after the new lens has been inserted, essentially after the cataract replacement portion of the surgery has been completed.

The present use can be combined with other therapies. Antibiotic therapy will likely be used after cataract surgery, such as antibiotic drops or sustained release antibiotic therapy (see U.S. Pat. No. 7,906,136), as the healthcare provider prescribes. Additionally, should the patient require additional anti-inflammatory medications for some reason, these are not contraindicated by the use of the present formulations. Also, some patients may need anti-glaucoma therapy after cataract surgery. These therapies are known in the art.

Another aspect of the present invention provides for use of a formulation consisting of dexamethasone in ATEC for the preparation of a medicament for the treatment of intraocular inflammation following cataract surgery wherein the single, fixed dosage amount is, for example, about 5 µL of about 342 µg, 517 µg, or 697 µg of dexamethasone.

Importantly, the present invention provides use of a formulation that treats an acute inflammatory response to a surgical event. By design it is formulated to deliver an immediate, high dose very quickly to give a quick response. The amount of dexamethasone released from the formulation then tapers off quickly to minimize the potential of any adverse events associated with the use of steroids. In clinical trials, this use resulted in positive outcome for humans following cataract surgery.

EXAMPLES

Example 1

In Vitro Release of Dexamethasone from Citrate Formulations

A series of in vitro experiments were conducted to measure the dexamethasone release kinetics from formulations of dexamethasone and citrate. Liquid formulations of dexamethasone (Dex) and triethyl O-acetyl citrate (ATEC) were made by weighing each component and mixing them together with ample stiffing to form a homogenous mixture (drug product). A volume of 5 µL of the following three separate formulations of Dex/ATEC drug product was used in the in vitro study:

342 µg/5 µL, Equivalent dose: 342 µg
517 µg/5 µL, Equivalent dose: 517 µg
697 µg/5 µL, Equivalent dose: 697 µg Five microliters (5 µL) of the drug product was placed in a 20 mL scintillation vial then a sufficient quantity (q.s.) of saline solution (0.9% NaCl, pH 6-8) added to bring the total volume to 10 mL. The vials containing the drug product in saline were incubated at 37° C. At each time point, the sample vials were removed from the incubator and cooled to room temperature. Aliquots of solution (5 mL) were removed from each vial and tested for dexamethasone concentration using ultra performance liquid chromatography. Five mL of fresh saline was added back to each test vial to maintain infinite sink conditions, and the sample vials placed back into the incubator at 37° C. Aliquots were removed, as just described, and tested on days 1, 3, 7 and weekly thereafter for dexamethasone release. This drug release measurement approach is referred to as the 5/10 saline drug release method, because the total volume was 10 ml and the amount removed and replaced for testing was 5 mL. The in vitro Dex average release from the drug product is shown in Table 1 (see also FIG. 1):

TABLE 1

Dexamethasone Average Percent Release in 10 mL Saline

| Time (Days) | Ave. % Total Dex Released | SD | % RSD |
| --- | --- | --- | --- |
| Drug Product 342 µg Dex | | | |
| 1 | 44.6 | 1.8 | 4.0 |
| 3 | 71.1 | 3.0 | 4.2 |
| 7 | 97.3 | 2.8 | 2.9 |
| Drug Product 517 µg Dex | | | |
| 1 | 30.5 | 0.9 | 2.8 |
| 3 | 48.3 | 1.6 | 3.3 |
| 7 | 70.6 | 4.1 | 5.9 |
| 14 | 87.0 | 2.6 | 3.0 |
| 21 | 98.7 | 2.2 | 2.2 |
| Drug Product 697 µg Dex | | | |
| 1 | 23.5 | 1.7 | 7.1 |
| 3 | 40.9 | 3.3 | 8.1 |
| 7 | 59.5 | 3.3 | 5.5 |
| 14 | 76.9 | 2.8 | 3.7 |
| 21 | 90.9 | 4.1 | 4.5 |
| 28 | 96.1 | 4.5 | 4.7 |
| 35 | 99.8 | 1.2 | 1.3 | n = 6 for each time point.

Figure 2:
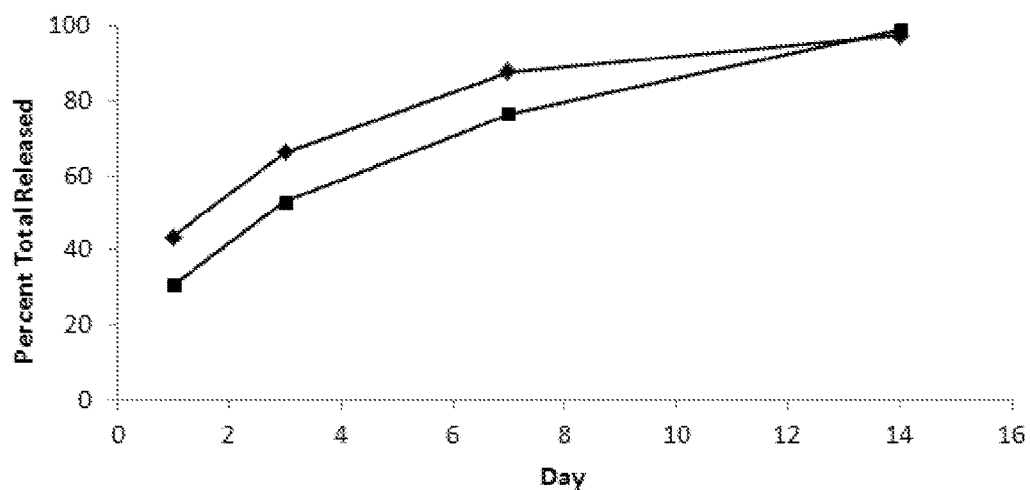
FIG. 2 shows the average in vitro Dex release from two formulations of Dex in ATEC, as percent release per day in a 20 mL saline infinite sink, n=6: ▲342 μg/5 μL; ■517 μg/5 μL.

In another in vitro test series, 342 µg/5 µL or 517 µg/5 µL (Dex in ATEC) were placed in vials and q.s. to 20 mL with 0.9% saline. Storage and testing were conducted as above, except that at each time point 15 mL withdrawn for sampling and was replaced with 15 mL of fresh saline. This method was named the 15/20 saline drug release method. The release of Dex from the drug product is shown in Table 2 (see also FIG. 2):

TABLE 2

Dexamethasone Average Percent Release in 20 mL Saline

| Time (Days) | Ave. % Total Dex Released | SD | % RSD |
| --- | --- | --- | --- |
| Drug Product 342 µg Dex | | | |
| 1 | 43.49 | 0.42 | 0.97 |
| 3 | 66.20 | 0.37 | 0.56 |
| 7 | 87.73 | 0.72 | 0.82 |
| 14 | 97.36 | 0.74 | 0.76 |
| Drug Product 517 µg Dex | | | |
| 1 | 30.70 | 0.58 | 1.88 |
| 3 | 53.01 | 1.25 | 2.36 |
| 7 | 76.66 | 1.86 | 2.42 |
| 14 | 99.14 | 0.59 | 0.59 | n = 6 for each time point.

Figure 3:
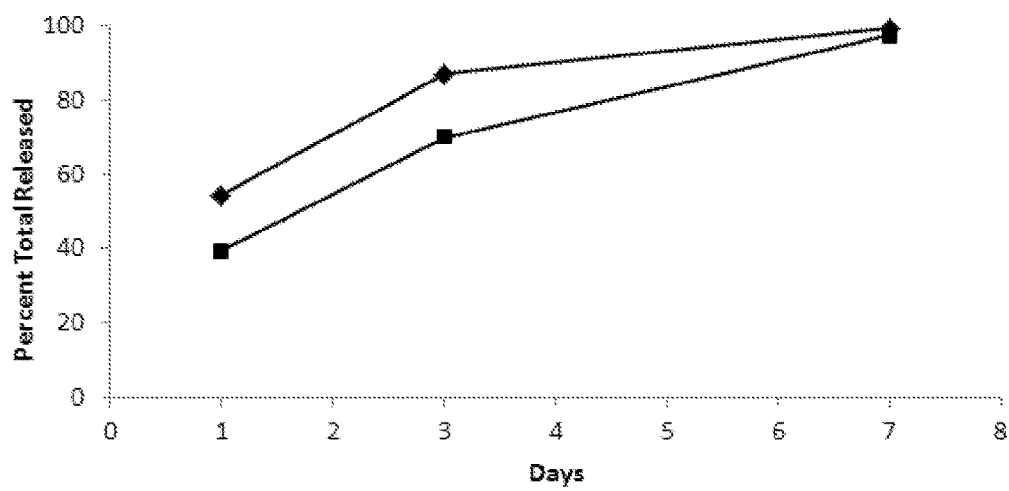
FIG. 3 shows the average in vitro Dex release from two formulations of Dex in ATEC, as percent release per day in 20 mL saline/β-cyclodextrin, n=6: ▲342 μg/5 μL; ■517 μg/5 μL.

To test in vitro release in an alternative buffer system, 342 µg/5 µL or 517 µg/5 µL (Dex in ATEC) were placed in vials and q.s. to 20 mL with a solution of 0.9% saline, 0.05% β-cyclodextrin. Storage and testing were conducted as above, except that at each time point 10 mL withdrawn for sampling and was replaced with 10 mL of fresh solution. This method was named the 10/20 saline/BCD drug release method. The release of Dex from the drug product is shown in Table 3 (see also FIG. 3):

TABLE 3

Dexamethasone Average Percent Release in 20 mL Saline/β-cyclodextrin

| Time (Days) | Ave. % Total Dex Released | SD | % RSD |
| --- | --- | --- | --- |
| Drug Product 342 µg Dex | | | |
| 1 | 54.40 | 2.35 | 4.33 |
| 3 | 87.04 | 7.67 | 8.81 |
| 7 | 99.23 | 0.95 | 0.96 |
| Drug Product 517 µg Dex | | | |
| 1 | 39.34 | 1.02 | 2.60 |
| 3 | 70.11 | 7.14 | 10.19 |
| 7 | 97.39 | 4.79 | 4.92 | n = 6 for each time point.

Figure 4:
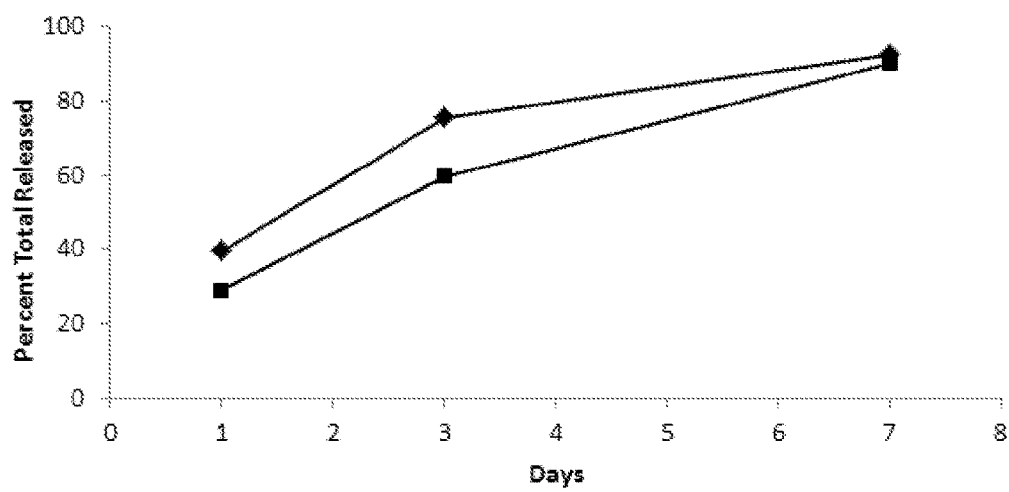
FIG. 4 shows the average in vitro Dex release from two formulations of Dex in ATEC as percent release per day in 20 mL saline/Tween-80, n=6: ▲342 μg/5 μL; ■517 μg/5 μL.

Another in vitro release in an alternative buffer system was undertaken, in which 342 µg/5 µL or 517 µg/5 µL (Dex in ATEC) were placed in vials and q.s. to 20 mL with a solution of 0.9% saline, 0.05% Tween-80. Storage and testing were conducted as above, except that at each time point 10 mL withdrawn for sampling and was replaced with 10 mL of fresh solution. This method was named the 10/20 saline/T80 drug release method. The release of Dex from the drug product is shown in Table 4 (see also FIG. 4):

TABLE 4

Dexamethasone Average Percent Release in 20 mL Saline/Tween-80

| Time (Days) | Ave. % Total Dex Released | SD | % RSD |
| --- | --- | --- | --- |
| Drug Product 342 µg Dex | | | |
| 1 | 39.69 | 3.29 | 8.28 |
| 3 | 75.71 | 10.23 | 13.52 |
| 7 | 92.44 | 5.70 | 6.16 |
| Drug Product 517 µg Dex | | | |
| 1 | 29.06 | 4.08 | 14.05 |
| 3 | 59.77 | 11.86 | 19.84 |
| 7 | 90.14 | 10.00 | 11.10 | n = 6 for each time point.

Example 2

In Vivo Release of Dexamethasone from Citrate

Figure 6:
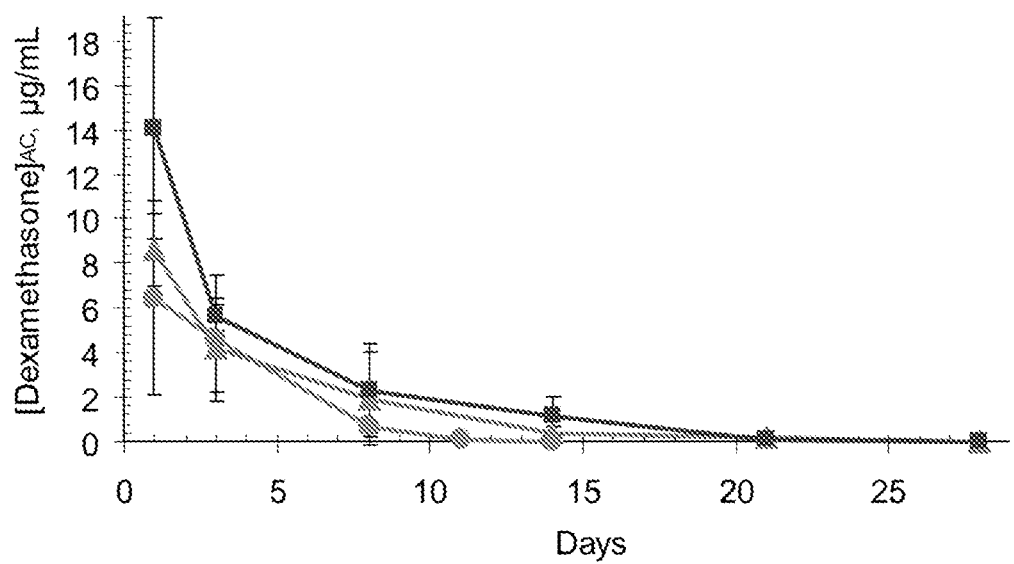
FIG. 6 shows in vivo pharmacokinetic release of dexamethasone into the aqueous humor of rabbit eyes following injection of 5 μL into the anterior chamber of one of three different formulations of dexamethasone in ATEC: ●342 μg/5 μL; ▲517 μg/5 μL; ■697 μg/5 μL. The data demonstrate that dexamethasone was released for 11 to 21 days.

Liquid formulations of dexamethasone and ATEC were made by weighing each component and mixing them together with ample stiffing to form a homogenous mixture, a uniformed blend. Dexamethasone, USP micronized, GMP manufacturing, is commercially available (e.g., Hawkins Pharmaceutical Group, Minneapolis, Minn.; Pharmacia Upjohn, Kalamazoo, Mich.), with a certificate of analysis. Additional tests for identity and purity of dexamethasone were undertaken using infrared absorption and HPLC. ATEC, NF, is available commercially (e.g., from Vertellus Performance Materials Inc., Greensboro, N.C.) with a certificate of analysis. Additional testing for identity and purity were undertaken. The formulations were either 6%, 9% or 12% dexamethasone, such that each 5 µL dose contained 342

µg, 517 µg or 697 µg dexamethasone. Using a 30 gauge needle, a single dose of 5 µL was injected under humane conditions into the anterior chamber of the eyes of rabbits. Subsequently, samples of the aqueous humor of treated eyes were collected (generally about 100 µL to 150 µL in volume), pooled, concentrated 10-fold, and analyzed by liquid chromatography-mass spectrometry (LCMS) to afford the level of dexamethasone released into the aqueous humour. This drug release study was named the in vivo aqueous humor Dex release study. The sampling days and results are shown in FIG. 6. Dexamethasone was released for about 11 to about 21 days. One skilled in the art can readily extrapolate the sustained release profile from FIG. 6.

Example 3

Use of Sustained Release Dexamethasone Post Cataract Surgery

A Phase II post-cataract surgery inflammation study was undertaken to compare three dosage forms of short-term sustained release dexamethasone. This was a multicenter, randomized, double-masked, dose ranging study for efficacy and safety. The human patients were over 40 years of age, having visual acuity potential greater than 20/30 in the study eye and having a corneal endothelial cell count of ≥2000 cells/mm² underwent unilateral cataract surgery by phacoemulsification. Patients eye were excluded from the study who had (a) used any ocular, topical or oral corticosteroids within 7 days prior to day 0; (b) received a periocular corticosteroid injection in the study eye in the 3 months prior to screening; (c) used topical NSAIDs in the study eye within 15 days prior to screening; or (d) received any intravitreal corticosteroid delivery vehicle (e.g., Restisert or Ozurdex), in the study eye.

Dexamethasone in ATEC, prepared as a mixture as in Example 2, was supplied with a fill volume of 0.5 mL and packaged in a 2 mL glass vial, sealed with a rubber stopper and an aluminum seal. Each vial was intended to be used only once. The formulations were sterile, preservative-free suspensions; sterilization was accomplished using E-beam at 28 ±3 kGy after vial fill. Particle size % volume-size was 10%<10.0 µm, 50%<30.0 µm, 90%<90 µm. SOP for product content, uniformity, endotoxin, pH, sterility, etc. were followed. Dexamethasone release in saline from the 697 µg/5 µL, Dex, average value n=6: 24 hours: 10%-50% (ave. 20.4%), 3 days: 30%-70% (ave. 41.0%), 7 days: 45%-90% (ave. 57.4%). Dexamethasone release in saline from the 517 µg/5 µL, Dex, average value n=6: 24 hours: 15%-55% (ave. 27.6%), 3 days: 35%-75% (ave. 47.1%), 7 days: 50%-95% (ave. 66.8%). Dexamethasone release in saline from the 342 µg/5 µL, Dex, average value n=6: 24 hours: 15%-55% (ave. 39.2%), 3 days: 40%-80% (ave. 62.4%), 7 days: >50% (ave. 89.1%).

Osmolality was tested by incubating a 5 µL aliquot in 4.5 mL or 0.45% saline at 37° C. overnight, then samples were allowed to cool to room temperature and osmolality compared with 0.45% saline. The data observed was: 0.45% saline, pH 6.55, mOsm (milli Osmols per liter) 147; 342 µg/5 µL Dex, pH 6.56, mOsm 148; 517 µg/5 µL Dex, pH 6.50 mOsm 150; 697 µg/5 µL Dex, pH6.40, mOsm 174.

Figure 5:
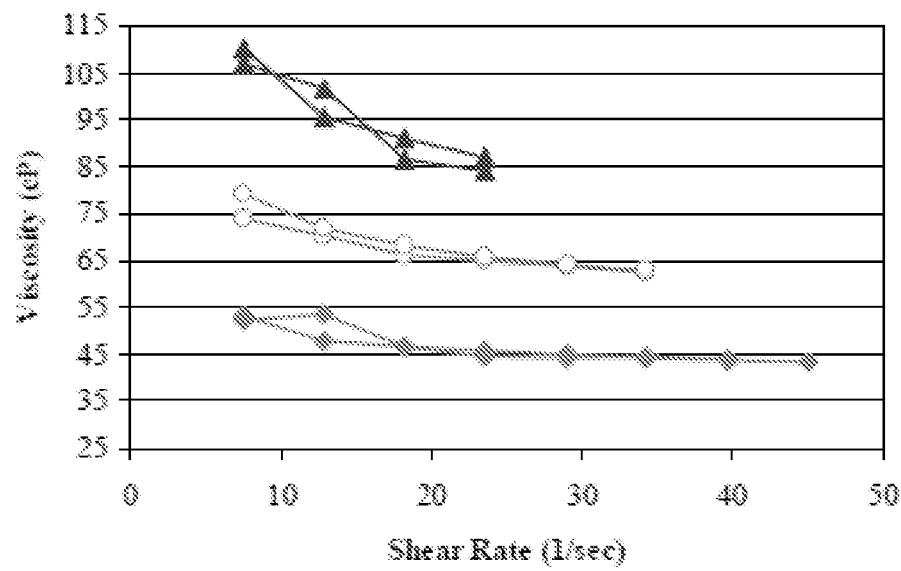
FIG. 5 presents data on the viscosities of three formulations of Dex in ATEC. ◆342 μg/5 μL; ○517 μg/5 μL; ▲697 μg/5 μL.

Viscosity was also measured at 25° C. At shear rates ranging from 7.5 to 23.55 sec-1, the viscosity of 697 µg/5 µL Dex ranged from 106.66 cp to 84.24 cp. At shear rates ranging from 7.50 to 34.28 sec-1, the viscosity of 517 µg/5 µL Dex ranged from 73.87 cP to 62.64 cP. At shear rates ranging from 7.50 to 45.00 sec-1, the viscosity of 342 µg/5 µL Dex ranged from 53.02 cP to 43.47 cP. From the viscosity data, the formulations showed characteristics of Non-Newtonian (pseudo-plastic) fluids. See also FIG. 5.

After the completion of cataract surgery, a single dose containing either 342 µg, 517 µg or 697 µg Dex in ATEC was delivered by injection using a disposable sterile insulin syringe that was used to withdraw and inject about 5 µL, using syringe loading and dosing guides to position the plunger to deliver a unit dose volume of 5 µL into the anterior chamber of the study eye. The amount of dexamethasone per patient was assigned at random. Anterior chamber cells (ACC) were graded as a score of 0 to 4, assessed by slit lamp biomicroscopy. Ocular and non-ocular safety was monitored through day 90.

Figure 7:
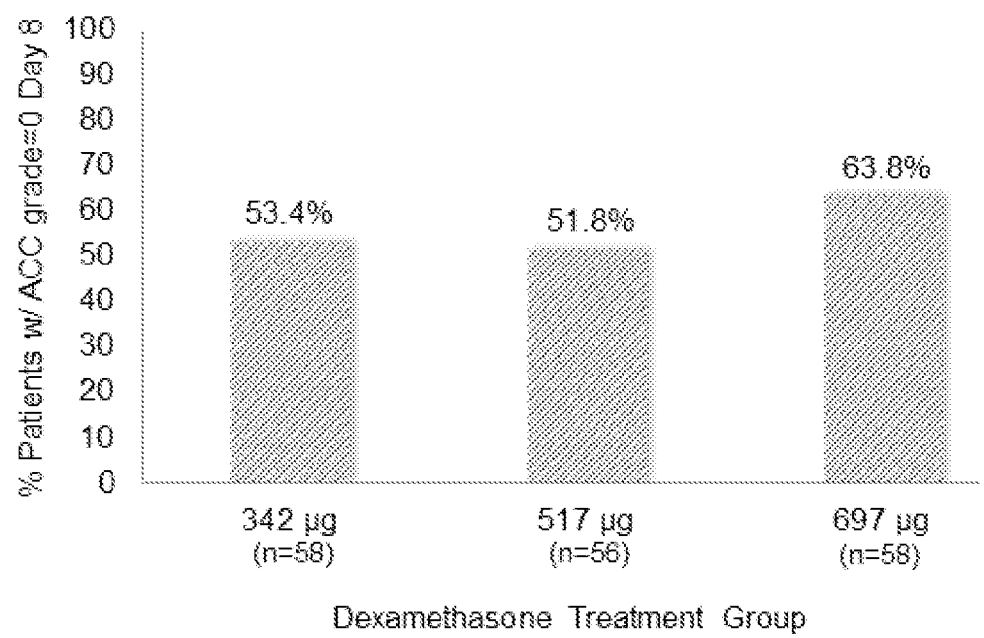
FIG. 7 shows the proportion of patients with ACC grade=0 at day 8 following cataract surgery and administration of a single 5 μL unit dose of one of three concentrations of Dex in ATEC, as indicated.
Figure 8:
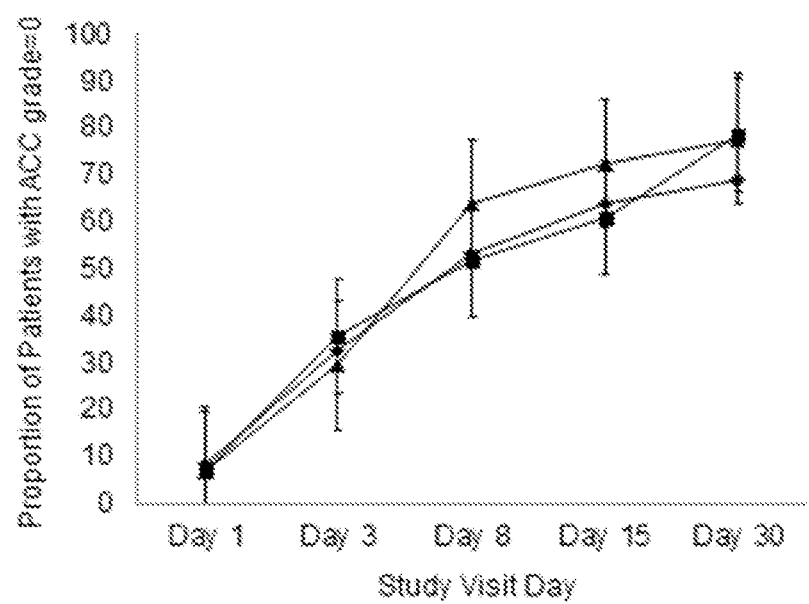
FIG. 8 shows the secondary endpoint in a Phase II clinical trial (of cataract surgery patients treated with a single administration of the formulations as in FIG. 7), as the proportion of patients with ACC Grade=0 over time. ◆342 μg/5 μL; ■517 μg/5 μL; ▲697 μg/5 μL. Vertical bars are ±1 standard error of the unadjusted mean. The last-observation-carried-forward (LOCF) method was used to impute missing data.

As a primary endpoint, the proportion of patients with ACC Grade=0 at day 8 was 53.4% /342 µg (n=58), 51.8% /517 µg (n=56), and 63.8%/ 697 µg (n=58). See FIG. 7. As a secondary endpoint, the proportion of patient with ACC Grade=0 over time is shown in FIG. 8. There was no statistically significant difference among the three treatment groups.

Regarding safety and efficacy, no patients suffered suprachoroidal hemorrhage or retinal detachment, and only on patient (in the 342 µg group) suffered endophthalmitis. The study eye serious adverse events were consistent with published serious adverse events following cataract surgery.

Example 4

Comparative Efficacy

Use of three formulations of dexamethasone in citrate (as described in Examples 2 and 3) was compared with standard anti-inflammatory eye drops therapy in reduction of anterior chamber inflammation.

For a comparison with steroidal Lotemax® (loteprednol 0.5%), data was collected in which the primary endpoint was reduction of anterior chamber inflammation (ACI), the sum of anterior chamber cells (ACC=0-5 cells* and flare=0) in the post-operative eye:

|  | loteprednol QID | Vehicle |
|---|---|---|
| Trial 1 - Visit Days 7-12** | 43% | 18% |
| Trial 2 - Visit Days 7-12** | 34% | 17% |

* For ACC grading, this endpoint is equivalent to ACC Grade 0 and 1 for IBI-10090.
**The Target Date was Day 8, but allowed patients to receive the dose up to Day 12.

For comparison with steroidal Durazol® (difluprednate 0.05%), data was collected in which the primary endpoint was the proportion of subjects with an anterior chamber cell grade of "0" on Day 8:

|  |  | difluprednate QID | Vehicle |
|---|---|---|---|
| Trial 1 | Day 3 | 7.3% | 0% |
|  | Day 8 | 23.6% | 10.3% |
|  | Day 15 | 45.0% | 14% |
| Trial 2 | Day 3 | 1.9% | 1.7% |
|  | Day 8 | 21.2% | 5.3% |
|  | Day 15 | 36.5% | 8.8% |

For comparison with an NSAID eye drop, Acuvail® (ketorolac 0.4%) the primary endpoint was the proportion of patients with clearing of anterior chamber inflammation (summed ocular inflammation score=0):

|  |  | ketorolac BID | Vehicle |
|---|---|---|---|
| Trial 1 | Day 8 | 29% | 16% |
|  | Day 14 | 46% | 25% |
| Trial 2 | Day 8 | 33% | 17% |
|  | Day 14 | 58% | 25% |

For comparison with another NSAID eye drop, Bromday® (bromfenac 0.09%), the primary endpoint was the sum of anterior chamber cell (ACC=0-5 cells)* and flare equal to zero at Day 15:

|  |  | bromfenac 0.09% | Vehicle |
|---|---|---|---|
| Trial 1 | Day 8 | 33.8% | 13.3% |
|  | Day 14 | 62.6% | 39.8% |
| Trial 2 | Day 8 | 38.6% | 21.9% |
|  | Day 14 | 65.8% | 47.9% |

*For ACC grading, this endpoint is equivalent to ACC Grade 0 and 1 for the injected dexamethasone in citrate. These numbers also included patients who were on additional anti-inflammatory drops.

For comparison with another brofenac NSAID eye drop, Prolensa® (bromfenac 0.07%), the primary endpoint was the proportion of patients with clearance of ocular inflammation (0 cell and no flare):

|  |  | bromfenac 0.07% | Vehicle |
|---|---|---|---|
| Trial 1 | Day 8 | 24.1% | 6.5% |
|  | Day 14 | 45.5% | 13.0% |
| Trial 2 | Day 8 | 30.0% | 12.7% |
|  | Day 14 | 45.5% | 27.3% |

Dosing schedule: Day before surgery, prior to surgery, once a day thereafter.

For comparison with another NSAID eye drop, Ilevro® (nepafenac 0.3%), the primary endpoint was the proportion of patients with clearance of ocular inflammation (0 cell and no flare) at Day 7:

|  |  | nepafenac 0.3% | Vehicle |
|---|---|---|---|
| Trial 1 | Day 3 | 11.4% | 10.7% |
|  | Day 7 | 34.1% | 18.8% |
|  | Day 14 | 68.4% | 34.0% |
| Trial 2 | Day 3 | 6.4% | 3.2% |
|  | Day 7 | 31.3% | 10.3% |
|  | Day 14 | 64.6% | 25.0% |

Dosing schedule: Day before surgery, prior to surgery, once a day thereafter.

Figure 9:
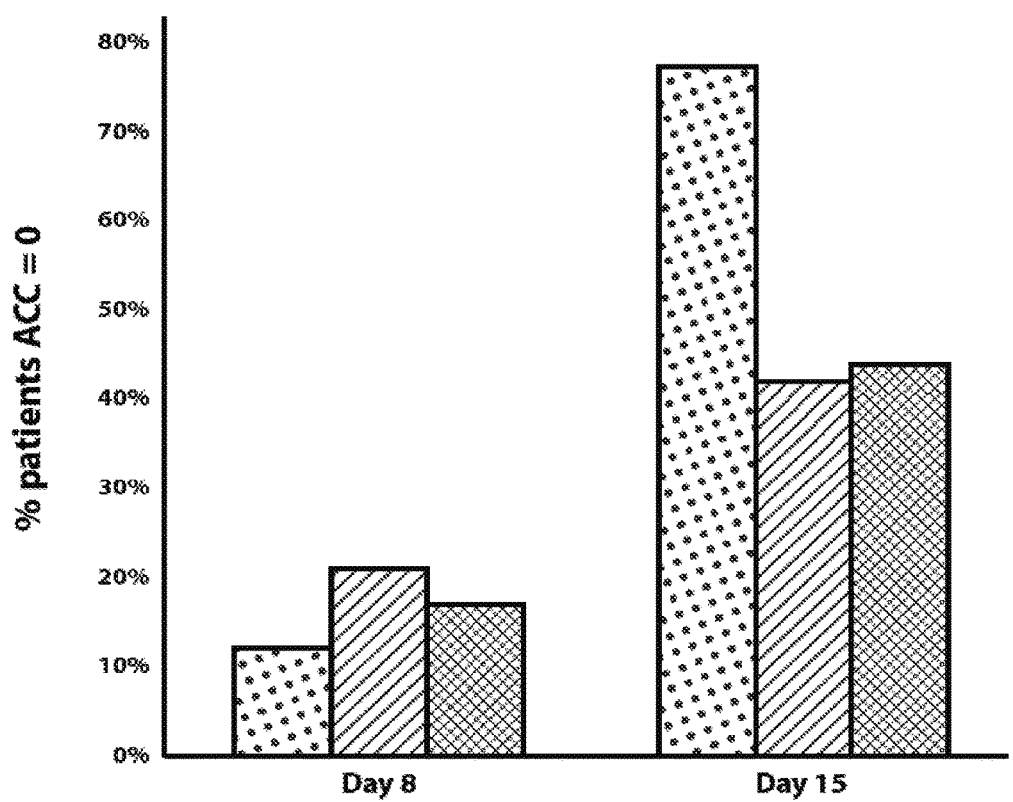
FIG. 9 is a graph showing the percent of patients exhibiting anterior chamber cell clearing in twenty-six human cataract surgery patients injected with dexamethasone in citrate, as described herein, compared with published data on anterior chamber cell clearing using two commercially available products: dexamethasone from Surodex® implants and difluprednate from Durezol® eye drops. Dots: dexamethasone in citrate; hatching: Surodex® implants; cross-hatching: Durezol® difluprednate eye drops.

An additional comparison was undertaken measuring anterior chamber cell clearing in human patients. A comparison graph is shown in FIG. 9, for anterior chamber cell clearing at Day 8 and Day 15, created using preliminary data in twenty-six patients treated with dexamethasone in citrate following cataract surgery as described herein, compared with published data for anterior chamber cell clearing using Durezol® difluprednate steroid eye drops and Surodex® PLGA-based sustained release-dexamethasone implant.

When data for commercially available drug products are compared with data for the injected formulations as described herein, it is clear that the efficacy provided by the instant embodiments is superior to other dosage forms and regimens.

We claim:

1. A method of treating inflammation of an eye following cataract surgery comprising the steps of:
   following completion of cataract surgery on the eye, administering by injecting into the eye a single dose of about 4 µL to about 6 µL of a formulation consisting essentially of about 517 µg dexamethasone in triethyl acetyl citrate;
   wherein said formulation releases said dexamethasone for at least 3 days as measured in saline solution under infinite sink conditions.

2. The method of claim 1, wherein the volume of said dose is about 5 µL.

3. The method of claim 1, wherein said formulation releases said dexamethasone for at least 7 days, as measured in saline solution under infinite sink conditions.

4. The method of claim 1, wherein said formulation releases said dexamethasone for at least 7 days, but no more than 35 days, as measured in saline solution under infinite sink conditions.

5. The method of claim 1, wherein said formulation retains at least 30% of said dexamethasone after 3 days, as measured in saline solution under infinite sink conditions.

6. The method of claim 1, wherein said single dose results in an anterior chamber cell count below 3 within 8 days of administration, when assessed by slit lamp microscopy.

7. The method of claim 1, wherein said single dose results in an anterior chamber cell count below 2 within 30 days of administration when assessed by slit lamp microscopy.

8. The method of claim 1, wherein said dose is injected behind the iris of the eye.

9. The method of claim 1, wherein said dose is injected into the anterior segment of the eye.

10. The method of claim 1, wherein said dose is injected into the anterior chamber of the eye.

11. The method of claim 8, wherein the volume of said dose is about 5 µL.

* * * * *